Figure 1:
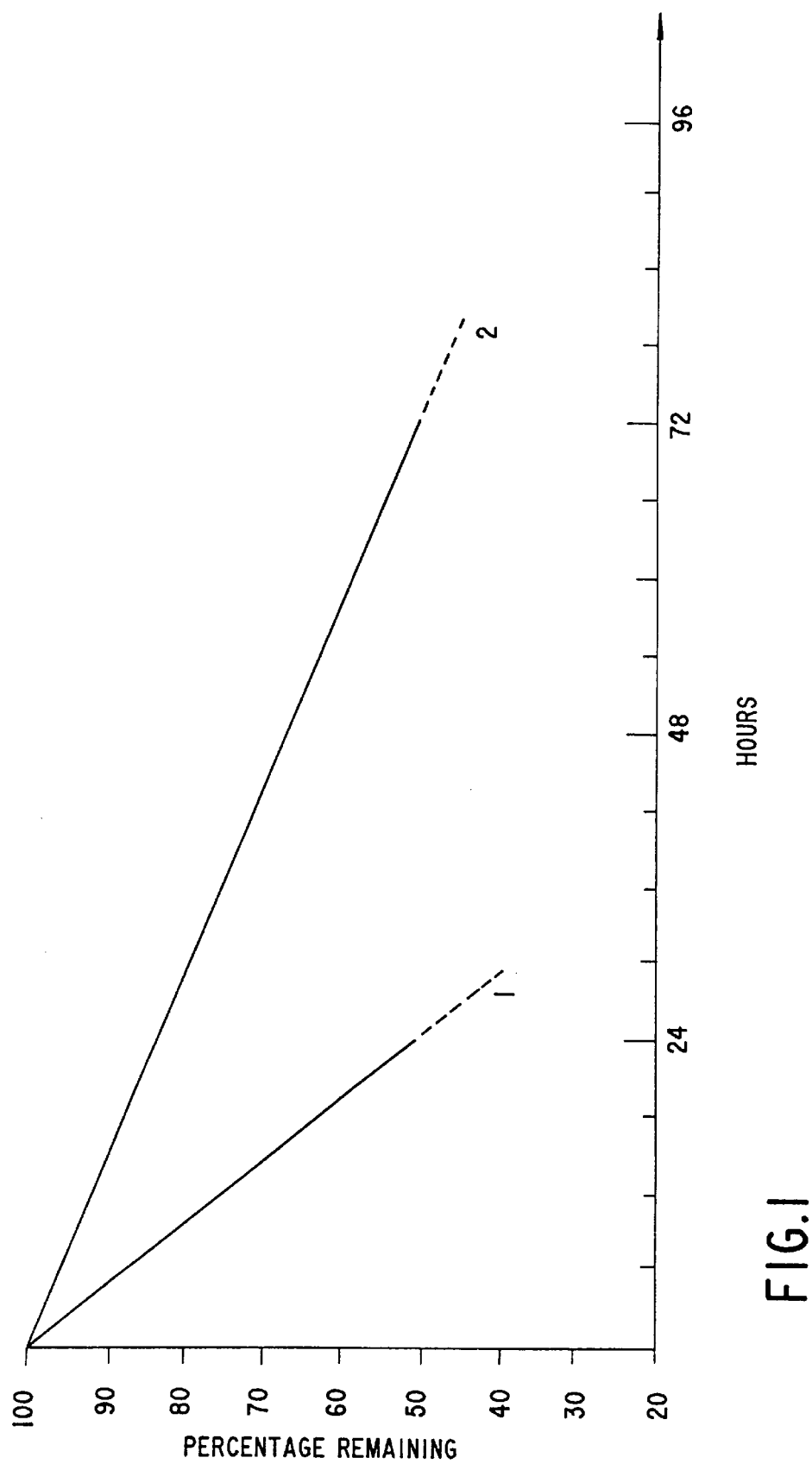

United States Patent [19]
Nofre et al.

[11] Patent Number: 5,997,933
[45] Date of Patent: *Dec. 7, 1999

[54] N-(3,3-DIMETHYLBUTYL)-L-ASPARTYL-D-α-AMINOALKANOIC ACID N-(S)-1-PHENYL-1-ALKANAMIDE USEFUL AS A SWEETENING AGENT

[76] Inventors: Claude Nofre, 119 Cours Albert Thomas, 69003 Lyons, France; Jean-Marie Tinti, 5 Impasse de Drelatiére, 69680 Chassieu, France

[*] Notice: This patent issued on a continued prosecution application filed under 37 CFR 1.53(d), and is subject to the twenty year patent term provisions of 35 U.S.C. 154(a)(2).

[21] Appl. No.: 08/980,306

[22] Filed: Nov. 28, 1997

Related U.S. Application Data

[62] Division of application No. 08/796,034, Feb. 5, 1997, Pat. No. 5,777,159.

[30] Foreign Application Priority Data

Feb. 7, 1996 [FR] France .................................. 96 01491

[51] Int. Cl.⁶ ........................................................ A23L 1/236
[52] U.S. Cl. ................................................ 426/548; 562/450
[58] Field of Search .............................. 562/450; 426/548

[56] References Cited

U.S. PATENT DOCUMENTS 5,286,509  2/1994  D'Angelo .

*Primary Examiner*—Michael L. Shippen
*Attorney, Agent, or Firm*—Armstrong, Westerman, Hattori, McLeland & Naughton

[57] ABSTRACT

The present invention has as subject compounds of formula:

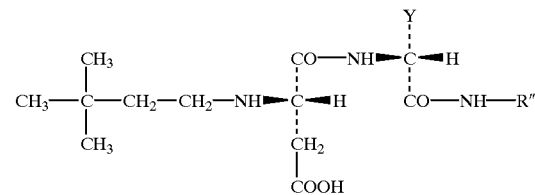

in which Y is $C_2H_5$, $(CH_3)_2CH$ or (R) $CH(OH)CH_3$, and R" is (S) $CH(C_2H_5)C_6H_5$, (S) $CH(CH_3)C_6H_5$ or (R) $CH(CH_2OCH_3)C_6H_5$. These compounds are useful as sweetening agents.

5 Claims, 2 Drawing Sheets

5,997,933

N-(3,3-DIMETHYLBUTYL)-L-ASPARTYL-D-α-AMINOALKANOIC ACID N-(S)-1-PHENYL-1-ALKANAMIDE USEFUL AS A SWEETENING AGENT

This is a division of application Ser. No. 08/796,034 filed Feb. 5, 1997, now U.S. Pat. No. 5,777,159.

The present invention relates to novel compounds derived from dipeptides, useful as sweetening agents, as well as to their method of preparation.

These novel compounds are particularly useful for sweetening a variety of products, especially drinks, foods, confectionery, pastries, chewing gums, hygiene products and toiletries, as well as cosmetic, pharmaceutical and veterinary products.

It is known that, in order to be usable on an industrial scale, a sweetening agent must possess firstly an intense sweetening potency, making it possible to limit the cost of use, and secondly a satisfactory stability, i. e. a stability compatible with the conditions of use.

Amongst the sweetening agents currently on the market, a dipeptide derivative L-aspartyl-L-phenylalanine methyl ester, known under the name of aspartame and having the following formula:

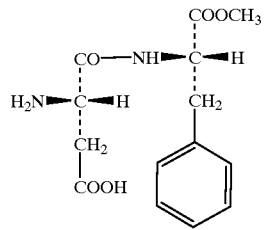

is the most widely used (U.S. Pat. No 3,475,403). The relatively weak sweetening potency of this compound is about 120 to 180 times that of sucrose on a weight basis. Despite its excellent organoleptic properties, the main disadvantage of this compound is that it is an expensive product on account of its relatively low sweetening intensity, and that it has a rather low stability under the usual conditions of use of sweetening agents, limiting its areas of industrial applications.

In the FR 92 13615 document, the Applicants have proposed sweetening agents of the following general formula:

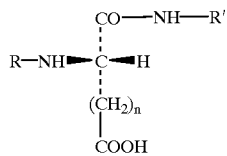

in which:

R is a saturated or non-saturated, acyclic, cyclic or mixed hydrocarbon group having from four to thirteen carbon atoms;

n is equal to 1 or 2; and

R' is represented by the following formula:

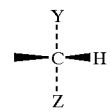

in which:

Y is selected from the groups $COOCH_3$, $COOC_2H_5$, $CH_3$, $CH_2OH$, $CON(CH_3)_2$, $C_6H_5$, 2-furyl, and H;

Z is selected from the groups $CH_2C_6H_5$, $C_6H_5$, n-$C_4H_9$, $COOCH_3$, $COOC_2H_5$, $COOC_3H_7$, COOfenchyl, and CONHR" in which R" is selected from the groups $CH_3$, $CH_2CH_3$, $CH_2CH_2CH_3$, $CH_2CH_2CH(CH_3)_2$, $CH(CH_3)COOCH_3$, $CH(c-C_3H_5)_2$, $CH(c-C_3H_5)C(CH_3)_3$, fenchyl, 2,6-dimethylcyclohexyl, 2,2,5,5-tetramethylcyclopentyl, and 2,2,4,4-tetramethyl-3-thietanyl.

One form of implementation described in the FR 92 13615 document covers the L-aspartic acid derivatives (n=1) of the following formula:

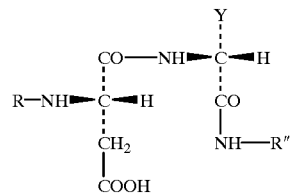

in which R, Y and R" are such as previously defined.

A preferred compound in this form of implementation of the invention is N-(3,3-dimethylbutyl)-L-aspartyl-N-(dicyclopropylcarbinyl)-D-alaninamide of formula:

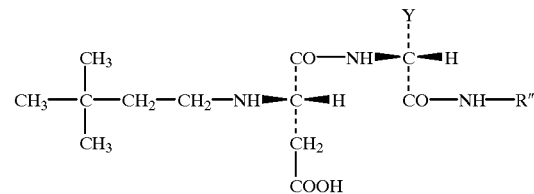

in which Y represents the methyl group and R" represents the dicyclopropylcarbinyl group which possesses a sweetening potency of 2,500 times that of sucrose on a weight basis with respect to a 2% sucrose solution.

It has been observed, and this constitutes the foundation of the invention, that it was possible to obtain novel sweetening compounds of the precited formula for suitably selected substituents Y and R", different from those provided in this prior document. Thus, when Y represents an ethyl, isopropyl or (R)-α-hydroxyethyl group and R" represents an (S)-α-ethylbenzyl, (S)-α-methylbenzyl or (R)-α-methoxymethylbenzyl group, novel compounds are obtained which possess excellent organoleptic qualities associated with a very high sweetening potency, up to 8,000 times the sweetening potency of sucrose on a weight basis. Furthermore, the stability of these compounds in acidic or neutral solution is distinctly higher than that of aspartame, which should have as effect to enlargen, with respect to aspartame, their possibilities of use in the food preparations.

The present invention has therefore as aim to provide novel sweetening agents responding to the following formula:

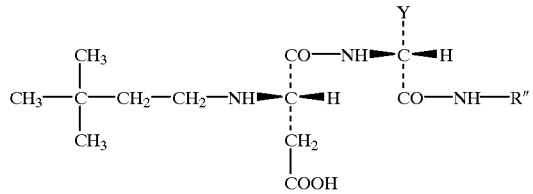

in which:

Y is $C_2H_5$, or $CH(CH_3)_2$ or (R) $CH(OH)CH_3$; and

R" is (S) $CH(C_2H_5)C_6H_5$, (S) $CH(CH_3)C_6H_5$ or (R) $CH(CH_2OCH_3)C_6H_5$.

The compounds responding to a particularly advantageous form of implementation of the invention are the N-(3,3-dimethylbutyl)-L-aspartyl-D-α-aminobutyric acid N—(S)-1-phenyl-1-propanamide of formula:

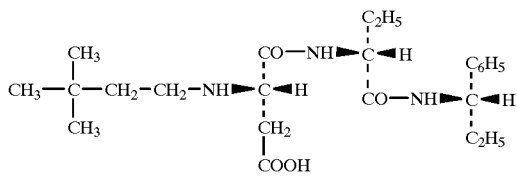

which has a sweetening potency of about 8,000 times that of sucrose on a weight basis with respect to a 2% sucrose solution, the N-(3,3-dimethylbutyl)-L-aspartyl-D-valine N—(S)-1-phenyl-1-propanamide of formula:

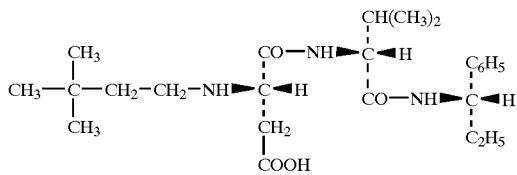

which has a sweetening potency of about 3,000 times that of sucrose on a weight basis with respect to a 2% sucrose solution;

the N-(3,3-dimethylbutyl)-L-aspartyl-D-α-aminobutyric acid N—(S)-1-phenyl-2-methoxy-1-ethanamide of formula:

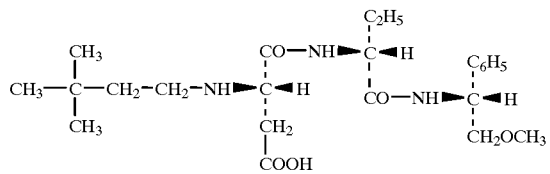

which has a sweetening potency of about 4,000 times that of sucrose on a weight basis with respect to a 2% sucrose solution; and the N-(3,3-dimethylbutyl)-L-aspartyl-D-valine N—(S)-1-phenyl-2-methoxy-1-ethanamide of formula:

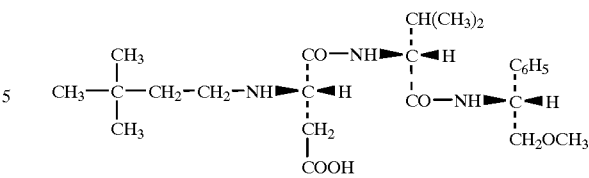

which has a sweetening potency of about 4,000 times that of sucrose on a weight basis with respect to a 2% sucrose solution.

Moreover, it has been demonstrated that the stability of these characteristic compounds of the invention is distinctly higher than that of aspartame under the common conditions of use for the food preparations. This advantage is all the more important because one of the limits of the use of aspartame in certain food preparations originates from its very low stability in media near to neutrality, i.e. for values of pH of about 7, values of pH which are frequently encountered in products such as dairy products, pastries or other preparations needing a high cooking temperature.

It has also been demonstrated that the stability of the compounds of the invention is further improved in acidic media at pH values of about 3, which correspond to pH values of soft drinks which constitute one of the major applications of sweetening agents.

Thus, by a study of accelerated ageing by prolonged heating an aqueous solution at pH 3 at 70° C., it has been shown that one of the characteristic compounds of the invention, the N-(3,3-dimethylbutyl)-L-aspartyl-D-α-aminobutyric acid N—(S)-1-phenyl-1-propanamide, possesses a half-life of about 72 hours. By way of comparison, the half-life of aspartame under the same conditions is only about 24 hours, which corresponds to a stability about 3 times greater for the compound according to the invention.

A same study of accelerated ageing at pH 7 has shown that the same compound, the N-(3,3-dimethylbutyl)-L-aspartyl-D-α-aminobutyric acid N—(S)-1-phenyl-1-propanamide, possesses a half-life of about 12 days, while the half-life of aspartame under the same conditions is only 10 minutes, which corresponds to a stability about 1,700 times greater for the compound according to the invention. Comparable results have been obtained for the other characteristic compounds of the invention.

From the fact of their high sweetening potency, another advantage of the compounds of the invention compared to aspartame is to allow, in their application to food products, the use of very low quantities of active agent. It is therefore for example that it is possible to replace, in one liter of soft drink, 550 mg of aspartame by about 20 mg of the N-(3,3-dimethylbutyl)-L-aspartyl-D-α-aminobutyric acid N—(S)-1-phenyl-1-propanamide of the invention, and to therefore reduce by about 27 times the quantities of sweetening agent consumed, always in maintaining the identical organoleptic qualities.

The sweetening agents of the present invention may be added to any edible product to which it is desired to give a sweet taste, provided that it is added in sufficient proportions to attain the level of sweetness desired. The optimal use concentration of the sweetening agent will depend upon a variety of factors such as, for example, the sweetening potency of the sweetening agent, the conditions of storage and use of the products, the particular constituents of the products and the level of sweetness desired. Any qualified person can easily determine the optimal proportion of sweetening agent which must be employed in order to obtain an edible product by carrying out routine sensory analyses. The sweetening agents of the present invention is, in general, added to the edible products in proportions, according to the sweetening potency of the compound, ranging from 5 mg to 50 mg of sweetening agent per kilogramme or per liter of edible product. The concentrated products will obviously contain greater quantities of sweetening agent, and will then be diluted following the final intentions of use.

The sweetening agents of the present invention may be added in the pure form to products to be sweetened, but because of their high sweetening potency they are generally mixed with an appropriate carrier or bulking agent.

Advantageously, the appropriate carriers or bulking agents are selected from the group consisting of polydextrose, starch, maltodextrins, cellulose, methylcellulose, carboxymethylcellulose and other derivatives of cellulose, sodium alginate, pectins, gums, lactose, maltose, glucose, leucine, glycerol, mannitol, sorbitol, sodium bicarbonate, phosphoric, citric, tartaric, fumaric, benzoic, sorbic and propionic acids and their sodium, potassium and calcium salts, and equivalents thereof.

The sweetening agent of the invention may, in an edible product, be employed as the only sweetening agent, or in combination with other sweetening agents such as sucrose, corn syrup, fructose, sweet dipeptide analogues or derivatives (aspartame, alitame), neohesperidin dihydrochalcone, hydrogenated isomaltulose, stevioside, the L sugars, glycyrrhizin, xylitol, sorbitol, mannitol, acesulfame-K, saccharin and its sodium, potassium, ammonium and calcium salts, cyclamic acid and its sodium, potassium and calcium salts, sucralose, monellin, thaumatin and equivalents thereof.

The compounds of the present invention are prepared by a reductive N-alkylation consisting in condensing the dipeptide precursor of formula:

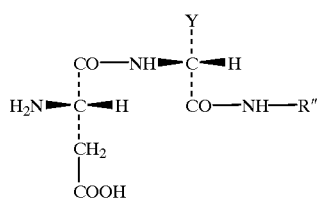

in which Y and R″ are such as defined previously, with 3,3-dimethylbutyraldehyde in the presence of a reducing agent. This reducing agent is either hydrogen under a relative pressure comprised between 1 and 3 bars and in the presence of a catalyst based on platinum or palladium following the procedure described in the WO 95/30689 document, or sodium cyanoborohydride following the procedure described in the FR 92 13615 document.

The dipeptide precursor of the above formula can easily be obtained by carrying out the basic principles of peptide synthesis: protection of the amino and carboxyl groups of the amino acid precursors and their deprotection, and classical methods of activation and peptide coupling.

These techniques are described in a detailed fashion in numerous publications, amongst which M. Bodanszky and A. Bodanszky, The Practice of Peptide Synthesis, Springer-Verlag, N.Y., 1984, 284 pp. may most particularly be cited.

The purification of the compounds of the invention is performed according to the standard techniques such as recrystallization and chromatography. Their structure and their purity have been checked by classical techniques (thin layer chromatography, high performance liquid chromatography, infrared spectroscopy, nuclear magnetic resonance, elementary analysis).

The sweetening potency of the compounds described in the examples has been evaluated by a group of eight experienced people. For this, the compound, in aqueous solution at varying concentrations, is compared, with respect to taste, to a control solution of sucrose of concentration 2%, 5%, or 10%. The sweetening potency of the test compound compared with sucrose then corresponds to the weight ratio between the compound and sucrose for equal sweetening intensity, i.e. when the sweet tastes of the solution of the test compound and the control solution of sucrose are considered by a majority of people to have the same sweetening intensity.

The stability of the compounds of the invention and aspartame was measured by determining, using high performance liquid chromatography (HPLC), the amount of product remaining after an accelerated ageing in acidic medium (phosphate buffer at pH 3) or in neutral medium (phosphate buffer at pH 7) and at the temperature of 70° C. The stability of the compound thus tested is evaluated by its half-life (time corresponding to 50% degradation).

The manner with which the invention may be carried out and the advantages which follow therefrom shall emerge better from the examples of implementation which follow.

EXAMPLES

Preparation of N-(3,3-dimethylbutyl)-L-aspartyl-D-α-aminobutyric acid N—(S)-1-phenyl-1-propanamide of formula:

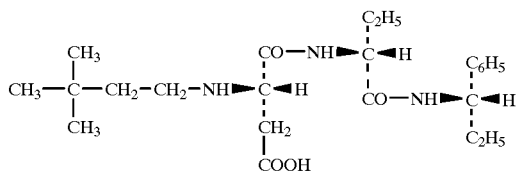

A mixture of 15 g (0.145 mole) of D-α-aminobutyric acid (Aldrich product No. 11,612-2) and 5.82 g (0.145 mole) of sodium hydroxide in 150 cm³ of water is cooled to 0° C. To this solution are simultaneously added, in a dropwise fashion, 24.38 g (0.145 mole) of benzyl chloroformate and 5.82 g (0.145 mole) of sodium hydroxide in aqueous solution (4N). Stirring is then maintained for 3 hours at 0° C. The reaction mixture is washed with diethyl ether (3×30 cm³) and then acidified by a solution of hydrochloric acid (6N) until a pH of about 1 is obtained. The white precipitate formed is separated off by filtration, washed with water then dried. 26 g (yield 75%) of N-benzyloxycarbonyl-D-α-aminobutyric acid are finally obtained whose melting point is 80° C.

To a solution of 3 g (13 mmoles) of the compound thus prepared in 50 cm³ of tetrahydrofuran cooled to −15° C. are successively added 1.28 g (13 mmoles) of N-methylmorpholine and 1.15 g (13 mmoles) of isobutyl chloroformate. After 2 minutes of stirring at this temperature, 1.71 g (13 mmoles) of (S)—1-phenyl-1-propanamine (previously prepared according to the document *J. Chem. Soc.,* 1940, pp. 336–8). The reaction mixture is slowly warmed up and then stirred for 2 hours at room temperature. The N-methylmorpholine hydrochloride precipitate is removed by filtration, then washed with 20 cm³ of tetrahydrofuran. The filtrates are concentrated to dryness in vacuo and the residue obtained is taken up into 150 cm³ of diethyl ether. The solution obtained is washed successively with a 0.1N solution of hydrochloric acid, a 5% solution of sodium carbonate then with water (3×30 cm³ for each washing). After drying of the ethereal solution over anhydrous sodium sulfate, the solution is concentrated to dryness in vacuo, which leads to 3.8 g of a white solid residue, N-benzyloxycarbonyl-D-α-aminobutyric acid N—(S)-1-phenyl-1-propanamide (yield 82%) whose melting point is 129° C. Its purity is checked by thin layer chromatography on silica gel G 60 (silica support Merck No. 1.05554), eluting with chloroform-acetone (9-1), and visualizing by the potassium dichromate-concentrated sulphuric acid mixture, Rf=0.45.

A solution of 3.6 g (10 mmoles) of N-benzyloxycarbonyl-D-α-aminobutyric acid N—(S)-1-phenyl-1-propanamide in 100 cm³ of methanol is submitted, in the presence of 350 mg of 10% palladium on activated charcoal (Fluka product No. 75990), to hydrogen under atmospheric pressure for 18 hours. After removal of the catalyst by filtration, the solution is concentrated to dryness in vacuo. 2.1 g (yield 91%) of D-α-aminobutyric acid N—(S)-1-phenyl-1-propanamide, in the form of an oily residue, is obtained. Its purity is checked by thin layer chromatography on silica gel G 60 (silica support Merck No. 1.05554), eluting with butanol-acetic acid-water (8-2-2), and visualizing with ninhydrin, Rf=0.57.

To a solution of 3.58 g (10 mmoles) of N-benzyloxycarbonyl-L-aspartic acid β-benzyl ester (Bachem product No. C-1350) in 50 cm³ of tetrahydrofuran cooled to −15° C. are successively added 1 g (10 mmoles) of N-methylmorpholine and 1.37 g (10 mmoles) of isobutyl chloroformate. After 2 minutes of stirring at this temperature, 2.1 g (10 mmoles) of the previously prepared D-α-aminobutyric acid N—(S)-1-phenyl-1-propanamide are added. The reaction mixture is slowly warmed up and then stirred for 2 hours at room temperature. The N-methylmorpholine hydrochloride precipitate is removed by filtration, and then is washed with 20 cm³ of tetrahydrofuran. The filtrates are concentrated to dryness in vacuo and the residue obtained is triturated in 50 cm³ of diethyl ether. The white solid formed is separated by filtration and is then washed again with 20 cm³ of diethyl ether. 5 g (yield 89%) of N-benzyloxycarbonyl-β-benzyl ester-L-aspartyl-D-α-aminobutyric acid N—(S)-1-phenyl-1-propanamide are thus obtained whose melting point is 130° C. Its purity is checked by thin layer chromatography on silica gel G 60 (silica support Merck No. 1.05554), eluting with chloroformacetone (8-2), visualizing with the sulfochromic mixture, Rf=0.64.

A solution of 5 g (8.9 mmoles) of N-benzyloxycarbonyl-β-benzyl ester-L-aspartyl-D-α-aminobutyric acid N—(S)-1-phenyl-1-propanamide in 100 cm³ of methanol is submitted, in the presence of 500 mg of 10% palladium on activated charcoal (Fluka product No. 75990), to hydrogen under atmospheric pressure for 18 hours. After removal of the catalyst by filtration, the solution is concentrated to dryness in vacuo. 2.4 g (yield 80%) of L-aspartyl-D-α-aminobutyric acid N—(S)-1-phenyl-1-propanamide are thus obtained in the form of a white solid. Its purity is checked by thin layer chromatography on silica gel G 60 (silica support Merck No. 1.05554), eluting with butanol-acetic acid-water (8-2-2), and visualizing with ninhydrin, Rf=0.50. Its melting point in this amorphous state is 195° C.

In a reactor equipped with a stirrer assuring a very good transfer of gaseous hydrogen into the liquid phase, are introduced, with stirring, in this order: 15 cm³ of a 0.1M aqueous solution of acetic acid, 26 mg of palladium on activated charcoal (Fluka Product No. 75990), 58 mg (0.57 mmole) of 3,3-dimethylbutyraldehyde of commercial origin (Aldrich No.35,990-4). 15 cm³ of methanol and 130 mg (0.38 mmole) of the previously prepared L-aspartyl-D-α-aminobutyric acid N—(S)-1-phenyl-1-propanamide.

After having purged the reactor with a current of nitrogen gas, the mixture is submitted to a hydrogenation at the relative pressure of 1–2 bars (0.1–0.2 MPa) at room temperature for 18 hours, then again for 8 hours after another addition of 19 mg (0.19 mmole) of 3,3-dimethylbutyraldehyde. The progress of the reaction is monitored by thin layer chromatography (TLC) on Silica gel 60 F254 support on aluminium sheets (Merck No.1.05554), eluting with butanol-acetic acid-water (8:2:2), and visualizing with ninhydrin: Rf 0.67.

The reaction is finally interrupted by purging the reactor with a current of nitrogen gas and separating the catalyst by filtration on a fine filter (0.5 μm). The solution is then concentrated by evaporation in vacuo and the white solid obtained is washed with about 50 cm³ of diethyl ether. 150 mg of the N—(3,3-dimethylbutyl)-L-aspartyl-D-α-aminobutyric acid N—(S)-1-phenyl-1-propanamide are finally obtained (yield 92%) in the form of a white powder of high purity (greater than 98% by H.P.L.C.) and whose melting point is 167° C.

Molecular formula: $C_{23}H_{37}N_3O_4$

NMR (200 MHz, 1H, ppm), DMSO D6: 0.80 (s, 15H), 1.33 (t, 2H), 1.67 (m, 4H), 2.4 (m, 4H), 3.54 (m, 1H), 4.30 (q, 1H), 4.70 (q, 1H), 7.22 (m, 1H), 7.28 (s, 5H), 8.35 (t, 2H).

High performance liquid chromatography on a Merck column of "Lichrospher 100 RP-18 endcapped" type, 244 mm in length, 4.6 mm in diameter, eluent: 65 mM ammonium acetate buffer—acetonitrile (70:30), flow: 1 ml/min, detector: refractometer, retention time: 16.1 min.

The sweetening potency of this compound corresponds approximately, on a weight basis, to 8,000 times that of sucrose by comparison with a 2% solution of sucrose, to 6,000 times that of sucrose by comparison with a 5% solution of sucrose and to 5,000 times that of sucrose by comparison with a 10% solution of sucrose.

By comparison with aspartame, an aqueous solution of 20 mg/L of this compound is equivalent in sweetening potency to a solution of 550 mg/L of aspartame, which corresponds to a sweetening potency about 27 times higher than that of aspartame.

Given in the annexed FIG. 1 is a comparative diagram of the stability curves of aspartame (curve 1) and of the N—(3,3-dimethylbutyl)-L-aspartyl-D-α-aminobutyric acid N—(S)-1-phenyl-1-propanamide of the present invention (curve 2) obtained during an accelerated ageing by heating their solutions in acidic medium at pH 3 (phosphate buffer) at 70° C. Under these conditions, the half-life of aspartame is 24 hours, while the half-life of the compound of the invention is about 72 hours, which corresponds to a stability which is three times greater in favour of the compound of the invention with respect to aspartame.

Figure 2:
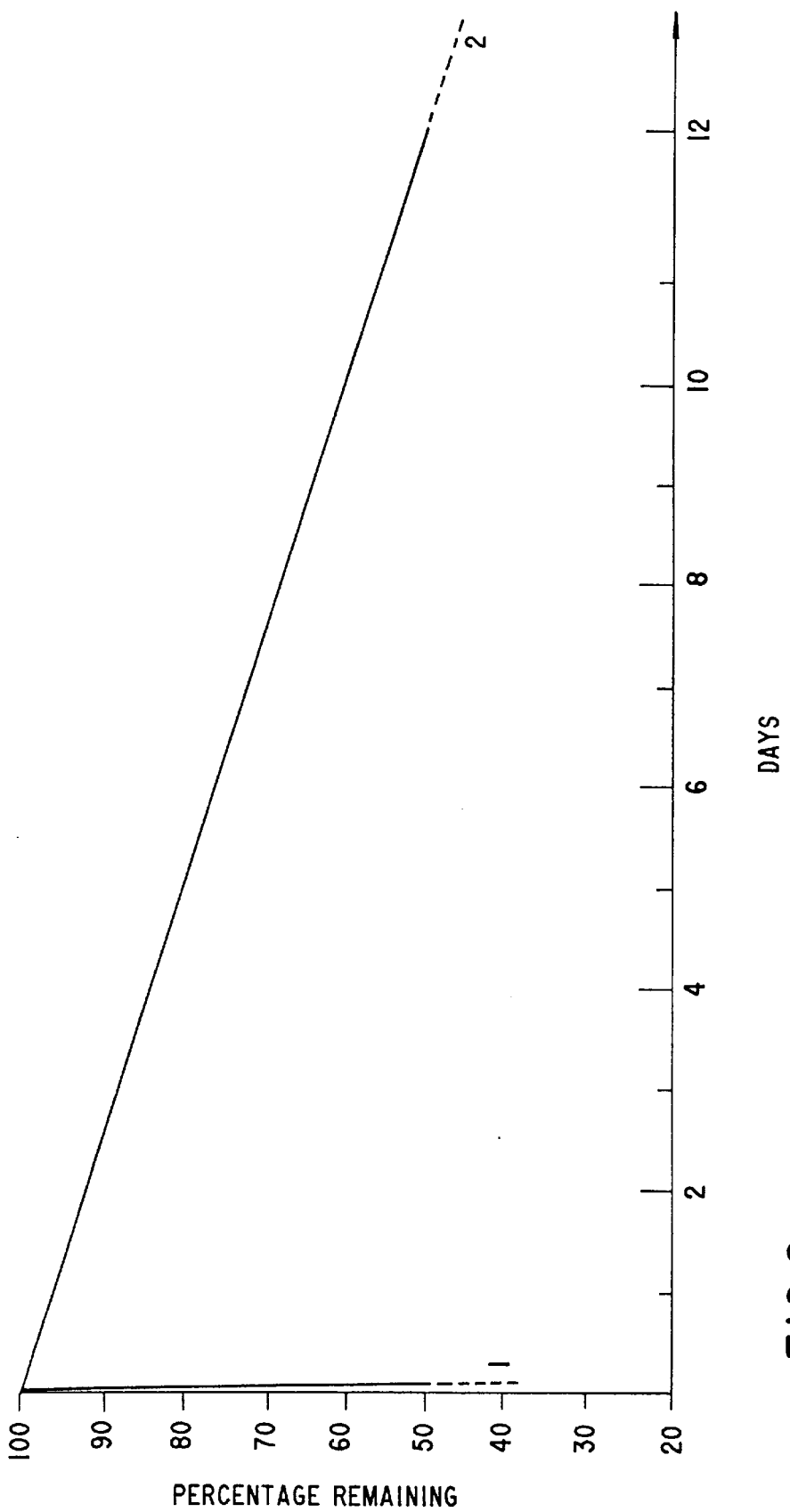

Given in the annexed FIG. 2 is a comparative diagram of the stability curves of aspartame (curve 1) and of the N-(3,3-dimethylbutyl)-L-aspartyl-D-α-aminobutyric acid N—(S)-1-phenyl-1-propanamide of the invention (curve 2) obtained during an accelerated ageing by heating their solutions in neutral media of pH 7 at 70° C. Under these conditions, aspartame is very little stable (half-life of 10 minutes) while the compound of the invention possesses a half-life of about 12 days, which corresponds to a stability which is about 1,700 times higher than that of aspartame.

The sweetening potency of other compounds according to the invention, obtained following an experimental protocol similar to that described above and that the person skilled in the art will easily find, is given in Table 1.

TABLE 1

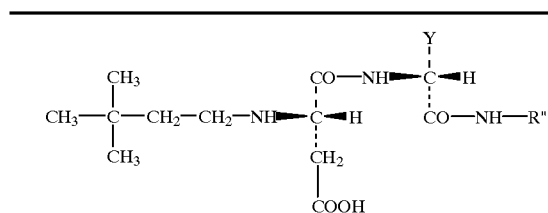

| Y | R" | Sweetening potency* |
|---|---|---|
| $C_2H_5$ | (S) $CH(C_2H_5)C_6H_5$ | 8,000 |
| $(CH_3)_2CH$ | (S) $CH(C_2H_5)C_6H_5$ | 3,000 |
| $C_2H_5$ | (S) $CH(CH_3)C_6H_5$ | 2,000 |
| $C_2H_5$ | (R) $CH(CH_2OCH_3)C_6H_5$ | 4,000 |
| $(CH_3)_2CH$ | (R) $CH(CH_2OCH_3)C_6H_5$ | 4,000 |

*The sweetening potency is given on a weight basis compared to a 2% solution of sucrose.

We claim:

1. A method of sweetening an edible product comprising the step of adding to said composition an effective sweetening amount of a compound of formula:

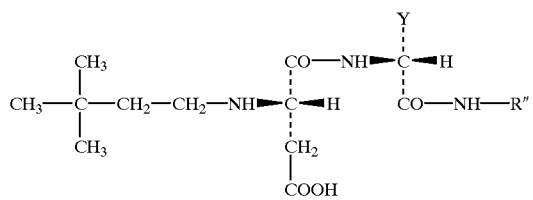

in which

Y is $C_2H_5$, $CH(CH_3)_2$ or (R) $CH(OH)CH_3$; and

R" is (S) $CH(C_2H_5)C_6H_5$, (S) $CH(CH_3)C_6H_5$ or (R) $CH(CH_2OCH_3)C_6H_5$.

2. The method according to claim 1, wherein the compound is N-(3,3-dimethylbutyl)-L-aspartyl-D-α-aminobutyric acid N—(S)-1-phenyl-1-propan-amide of formula:

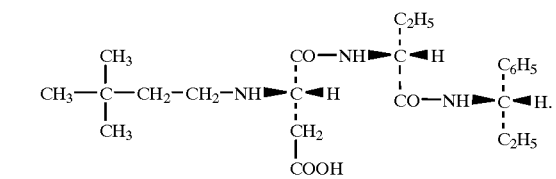

3. The method according to claim 1, wherein the compound is N-(3,3-dimethylbutyl)-L-aspartyl-D-valine N—(S)-1-phenyl-1-propanamide of formula:

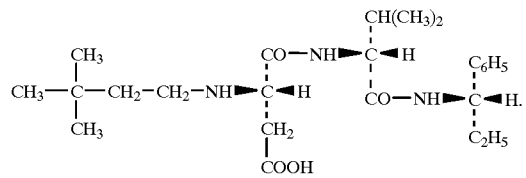

4. The method according to claim 1, wherein the compound is N-(3,3-dimethylbutyl)-L-aspartyl-D-α-aminobutyric acid N—(S)-1-phenyl-2-meth-oxy-1-ethanamide of formula:

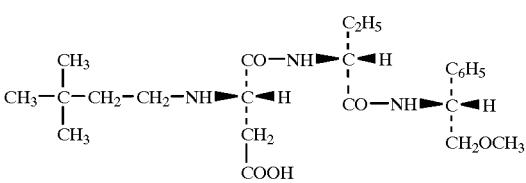

5. The method according to claim 1, wherein the compound is N-(3,3-dimethylbutyl)-L-aspartyl-D-valine N—(S)-1-phenyl-2-methoxy-1-ethanamide of formula:

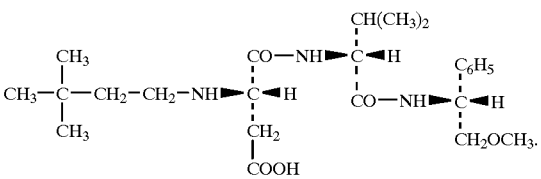

* * * * *